United States Patent [19]

Chen et al.

[11] Patent Number: 5,605,836
[45] Date of Patent: Feb. 25, 1997

[54] MODULAR METHOD AND DEVICE FOR THE EVALUATION OF THE ABILITY OF BIOCIDE TO PENETRATE BIOFILM

[76] Inventors: Chin-Yu Chen, 2F, No. 21, Lane 295, Ching Hsin St.; Woan-Jiun Swei, 2F, No. 21, Lane 295, Ching Shin St., both of Chung Ho City, Taiwan

[21] Appl. No.: 489,794

[22] Filed: Jun. 13, 1995

[51] Int. Cl.$^6$ .................................................. C12M 3/00
[52] U.S. Cl. ................................... 435/305.4; 435/287.4
[58] Field of Search .......................... 435/305.1, 305.4, 435/288.3, 31, 287.4; 422/102

[56] References Cited

U.S. PATENT DOCUMENTS

| | | | |
|---|---|---|---|
| 3,677,904 | 7/1972 | Fitzgerald | 435/305.4 |
| 4,912,037 | 3/1990 | Lemonnier | 435/34 |
| 5,061,621 | 10/1991 | Perlman | 435/30 |
| 5,348,885 | 9/1994 | Labarthe | 435/294 |

FOREIGN PATENT DOCUMENTS 0225748  8/1994  Japan ........................... C12M 1/00

*Primary Examiner*—David A. Redding

[57] ABSTRACT

A thickness modular device for use in the evaluation of the ability of a biocide to penetrate biofilms of varying thicknesses is disclosed. It comprises: (a) a petri dish including a horizontal base and a continuous sidewall mending vertically from the base; (b) a dish cover including a flat base with a top and underside for closing the dish; (c) an internal thickness module having a flat top and bottom surface and being positioned adjacent the horizontal base for producing depressions on a surface of a biofilm; and (d) a locking member for connecting in a locking relation the dish cover with the internal thickness module.

5 Claims, 4 Drawing Sheets

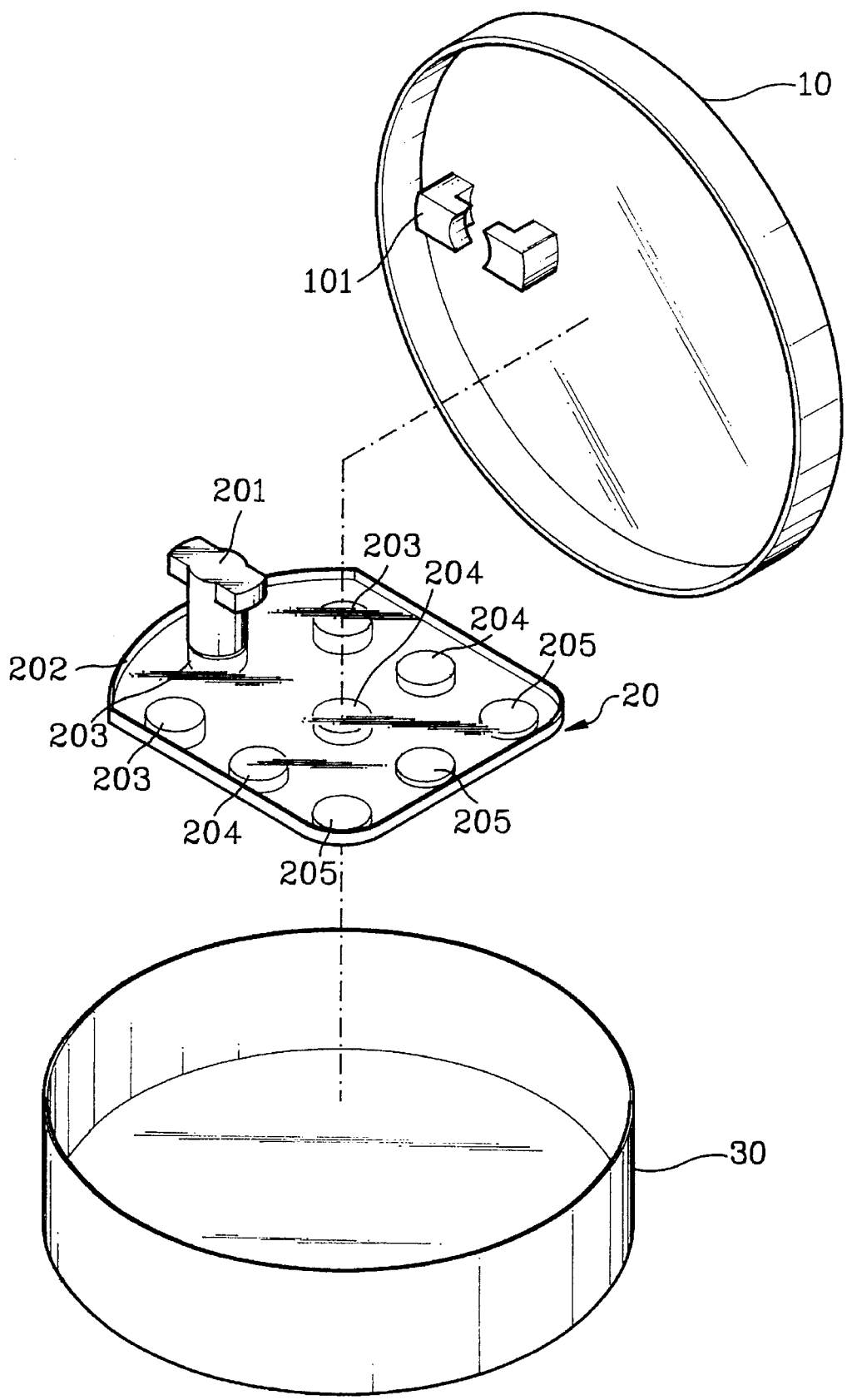
F I G. 2

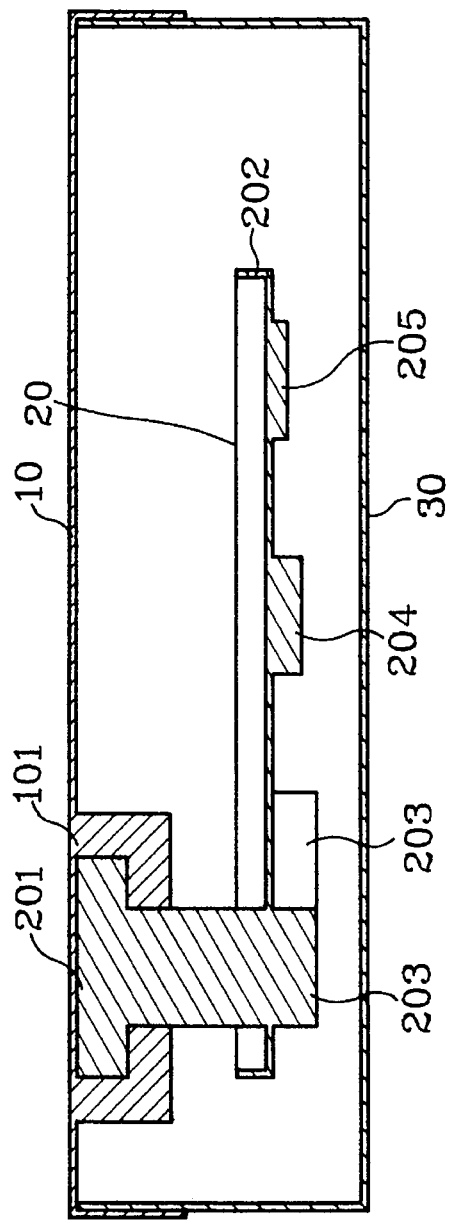
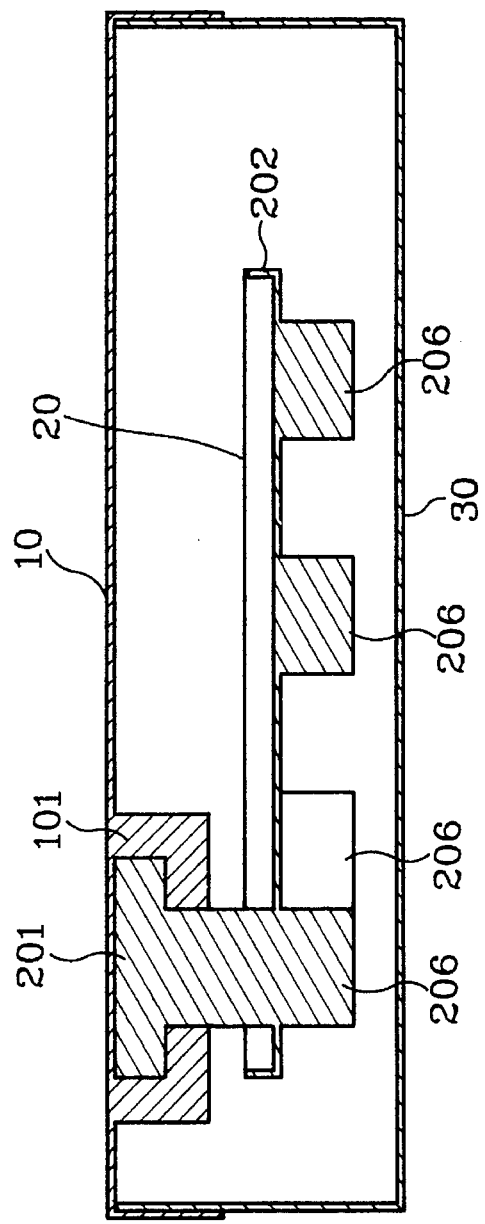

MODULAR METHOD AND DEVICE FOR THE EVALUATION OF THE ABILITY OF BIOCIDE TO PENETRATE BIOFILM

BACKGROUND OF THE INVENTION

Biofilms caused by various kinds microbiological contamination occur frequently in the conveying system of food processing plants, hospital devices such as urinary catheters, airplane fuel tanks and pipeline filters, waste water discharge lines of nuclear power plant heat exchanger s and so on. Such biofilms not only cause the affected pipelines to narrow, reducing their capacity and wasting energy but also could contribute to corrosion of the pipelines and endanger the entire system. In food processing plants, biofilms in conveying systems could additionally cause serious quality control problems. In hospitals, contaminated equipments and devices could infect patients. In aviation, once biofilms are developed in fuel lines, they could cause deterioration in the quality of the fuel and/or seriously affect air safety by damaging the integrity of the fuel lines by pitting the wall surface of the fuel lines so covered. Needless to say, how to combat the problems caused by biofilms is a very important and pressing problem.

At the present time, methods to control biofilm development consist of proper selection of materials for the various fluid conveying systems and the addition of biocides in the systems. Such biocides as the commercially available kathon, quaternary and glutaraldehyde are used in industrial plants; and such antibiotics as tobramycin, oxytetracycline, nystatin and erythromycin are used in hospitals. The effectiveness of these various biocides are expressed in terms of MIC-minimal inhibitory concentration. However, MIC is measured against microbiological concentrations in planktonic state only, and is quite irrelevant against microbes that have become sessile. It is not unusual to use biocides in concentrations of several hundred, even thousand times the, MIC to deal with sessile microbiological contamination. The main reason for this is that once biofilms are developed, they tend to act as barriers against the biocide. The thicker the biofilm, the stronger the barrier. Indeed, many research results have already indicated that the use of MIC values to indicate biocide effectiveness is misleading, because the MIC values can not represent the actual effect of biocides on microbiologicals that have developed biofilm.

In order to truly evaluate the effectiveness of a biocide against both planktonic and sessile microbes, a way must be developed to create biofilms of different thicknesses in the laboratory. At the present time, many different systems of biofilm reactors are being tested in the laboratories. These systems consists mainly of a reactor, a reactor feed, a pump and a set of lines. However, the systems are complicated, costly, and they are energy and time consuming to operate. They take up a lot of labortatory space. Furthermore, too many variables such as the shape and size of the reactor, the flow rate of the fluid, the speed of the pump and the fluid shear stress and reflux stress created against the inner wall of the fluid lines conspire to make the thickness of the developed biofilm inconsistent and unpredictable.

SUMMARY OF THE INVENTION

The present invention relates to a modular method and device for the evaluation of the ability of biocide to penetrate biofilm. Its purpose is to provide a quick and easy way to evaluate the ability of various biocides of different concentrations to penetrate biofilm. The method is economical as well as occupies minimum amount of space.

The purpose of the present invention is to overcome these technical difficulties by providing a simple and economical device for the creation of biofilms of different thicknesses.

Concurrently, the present invention also provides a means to establish an efficient and effective modular method to evaluate biocide effectiveness against biofilms based on our device.

BRIEF DESCRIPTION OF THE DRAWINGS

FIG. 2 is an internal exploded view of an example of the biofilm thickness modular device of the present invention.

FIG. 5 is plan view of an example of the device of the present invention.

FIG. 6 is plan view of another example of the device of the present invention.

DETAILED DESCRIPTION

Figure 1:
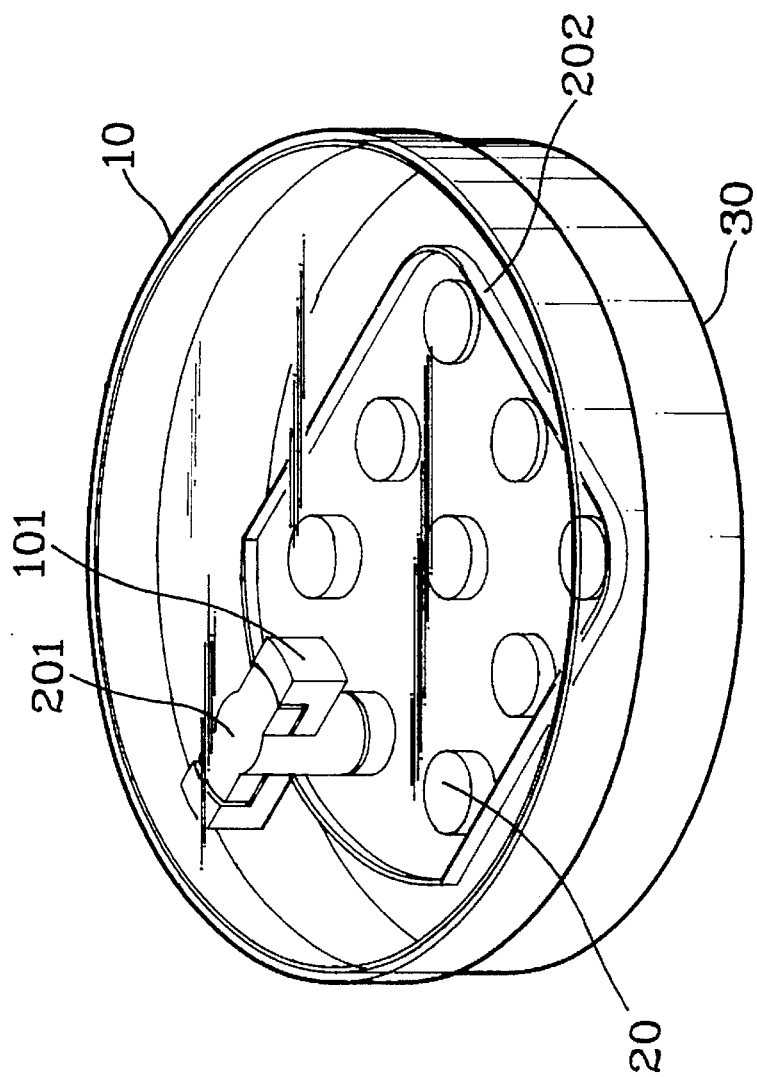
FIG. 1 is an external view of an example of the biofilm thickness modular device of the present invention.
Figure 4:
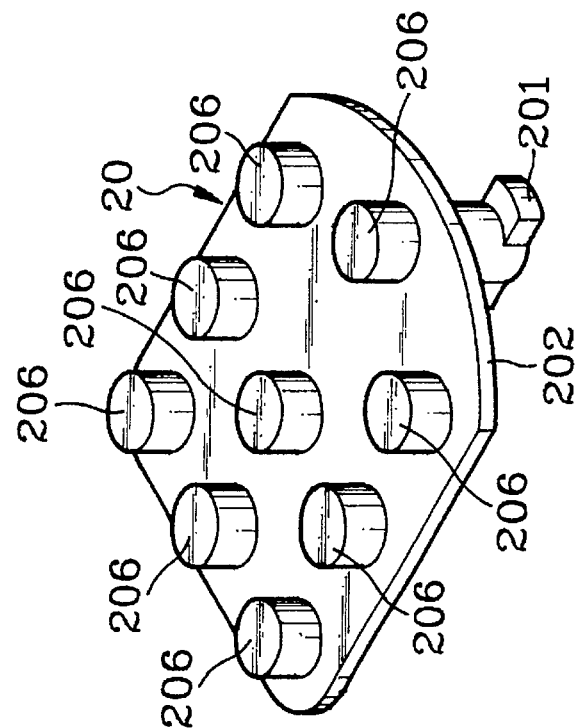
FIG. 4 is another external view of an example of the internal biofilm thickness module.
Figure 3:
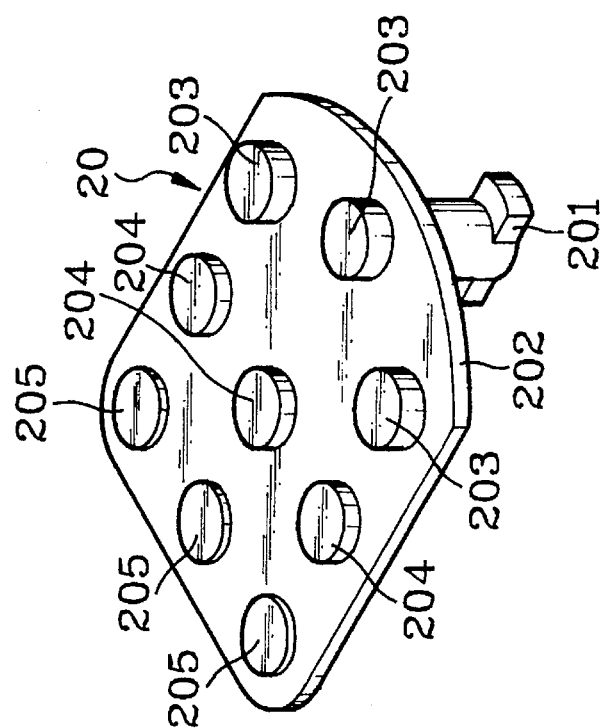
FIG. 3 is another external view of the biofilm thickness module.

Please review illustrations 1 and 2. They consist of an exterior perspective view as well as an interior perspective view of our device. The present invention consists of a petri dish cover (10), a petri dish bottom (30) and a thickness module (20). The cover (10) has a built-in female locking mechanism (101) located off-center on its underside which will lock onto a male locking mechanism (201) located at a similar position on the roof of the thickness module (20) through a twisting motion. To unlock, one simply twists the one against the other in the reverse direction (see illustrations 5 and 6). The thickness module is provided with a lip (202) around its rim to modulate against over-pouring of agar thus insuring the surface of the agar will not be torn up when the thickness module is removed. On the underside of the thickness module (20) are a number of protrusions of different heights (203), (204), (205) (see illustration 3) or of the same height (206) (see illustration 4). The heights of these protrusions correspond to the thickness of the biofilm that we wish to create. The best practical cross-section of these protrusions is round. After one pours agar into the petri dish bottom (30), presses the thickness module (20) with its attached petri dish cover (10) onto the surface of the agar and waits for it to set, then one could press down on the cover of the petri dish (10) and pull up the cover and the thickness module together. Then one detaches the cover (10) from the thickness module (20) by twisting one against the other, and places the cover (10) onto the petri dish bottom (30) which now contains agar with a smooth surface and a number of surface depressions of desired depths.

After different depths of depressions have been cast onto the smooth surface of the agar by using the first part of the present invention, which consists of the biofilm thickness module, one can then proceed to use the other part of the present invention, which is an evaluation procedure, for the effectiveness of biocides against biofilm. The evaluation procedure consists of the following steps:

(a) First, one takes a solution of cultured germ and runs it through a centrifuge, then pours out the suspension to obtain the slime below, which should be of a density of $10^8$ to one milliliter above. Take appropriate amount of the slime and fill in the modular holes that we have created in the agar surface mentioned above. (Agar will allow the germ to carry on its metabolic processes and develop biofilm of different thickness after some time).

(b) Prepare biocide of a given concentration. Pour a fixed amount of it in the petri dish containing the biofilm of different thicknesses as prepared according to (a) above. Allow it to act on the biofilm for a fixed amount of time under constant temperature in a static state.

(c) Pour out the biocide in the petri dish and perform an analysis of remaining activity with it. Compare the result with unused portion of the same biocide solution.

(d) Use sterile water to gently rinse the inside of the petri dish before testing the different thickness biofilms for microbiological activity. This way we can ascertain the effectiveness of a given concentration of biocide in penetrating different thickness of biofilm of a given microbiological entity.

Another experiment could be conducted in which different microbiological entities of the same biofilm thickness have been prepared in the same petri dish. With a similar procedure as described in (a), (b), (c) and (d) above, we can very quickly evaluate the effectiveness of a given concentration of biocide on penetrating different kinds of microbiologicals.

One can understand from above that our invention has the advantages of being easy and fast to operate, simple to set up in terms of equipment, small in size-taking up virtually no floor space and inexpensive, making it a practice solution to the biocide evaluation problem and a valuable invention for commercial use.

I claim:

1. A thickness modular device used in the evaluation of the ability of biocide to penetrate biofilms of varying thicknesses comprising:

a petri dish including a horizontal base and a continuous sidewall extending vertically from the base;

a dish cover including a flat base with a top surface and underside surface for closing the dish;

an internal thickness module having a flat top and bottom surface and being positioned adjacent the horizontal base for producing depressions on a surface of a biofilm;

a locking means for connecting in a locking relation the dish cover with the internal thickness module.

2. A thickness modular device as defined in claim 1 wherein the locking means is constructed such that the internal thickness module and the dish cover are connected and disconnected in locking relation through rotation of the module or the cover, and wherein the locking means is positioned off of the geometric center of the module and the cover.

3. A thickness modular device as defined in claim 1 wherein the locking means comprises a first and second part, the first part including a female locking mechanism attached to the underside surface of the dish cover, the second part including a male locking mechanism attached to the top surface of the module.

4. A thickness modular device as defined in claim 1 wherein the thickness module further includes a surface extending vertically from the edge of the top surface forming a lip, and a plurality of rod-shaped protrusions of the same length or of different lengths extending from the bottom surface of said module.

5. A thickness modular device as defined in claim 4 wherein the plurality of the rod-shaped protrusions are constructed in the form of circular rods.

\* \* \* \* \*